(12) United States Patent
Wildeman

(10) Patent No.: US 11,045,364 B2
(45) Date of Patent: *Jun. 29, 2021

(54) LOOP FASTENER MATERIAL FOR DIAPER AND RELATED METHOD

(71) Applicant: TIETEX INTERNATIONAL LTD., Spartanburg, SC (US)

(72) Inventor: Martin Wildeman, Spartanburg, SC (US)

(73) Assignee: TIETEX INTERNATIONAL LTD, Spartanburg, SC (US)

( * ) Notice: Subject to any disclaimer, the term of this patent is extended or adjusted under 35 U.S.C. 154(b) by 679 days.

This patent is subject to a terminal disclaimer.

(21) Appl. No.: 15/799,755

(22) Filed: Oct. 31, 2017

(65) Prior Publication Data

US 2018/0116881 A1    May 3, 2018

Related U.S. Application Data

(60) Provisional application No. 62/416,855, filed on Nov. 3, 2016.

(51) Int. Cl.
| | |
|---|---|
| *A61F 13/62* | (2006.01) |
| *D04B 21/16* | (2006.01) |
| *A61F 13/56* | (2006.01) |
| *D04B 21/02* | (2006.01) |
| *A61L 15/22* | (2006.01) |

(52) U.S. Cl.
CPC ........ *A61F 13/627* (2013.01); *A61F 13/5622* (2013.01); *A61L 15/225* (2013.01); *D04B 21/02* (2013.01); *D04B 21/165* (2013.01); *D10B 2501/0632* (2013.01); *D10B 2509/02* (2013.01)

(58) Field of Classification Search
CPC ...... A61F 13/62; A61F 13/622; A61F 13/627; A61F 13/5622; A61L 15/225; D04B 21/02; D04B 21/165; D04B 2501/0632; D04B 2509/02
See application file for complete search history.

(56) References Cited

U.S. PATENT DOCUMENTS

| | | | | |
|---|---|---|---|---|
| 5,707,707 | A * | 1/1998 | Burnes | D04B 21/04 428/95 |
| 6,869,660 | B2 * | 3/2005 | Wildeman | D04B 23/10 428/92 |
| 8,551,066 | B2 * | 10/2013 | Wildeman | A61F 13/5633 604/391 |
| 8,632,517 | B2 * | 1/2014 | Wildeman | D04B 21/02 604/391 |
| 10,517,778 | B2 * | 12/2019 | Wildeman | D04B 21/02 |
| 2004/0115388 | A1 * | 6/2004 | Wildeman | D04B 27/06 428/95 |
| 2005/0033490 | A1 * | 2/2005 | Abelard | G11B 20/10527 701/25 |

(Continued)

*Primary Examiner* — Michele M Kidwell
(74) *Attorney, Agent, or Firm* — J.M. Robertson, LLC

(57) ABSTRACT

A composite loop face fabric which incorporates a multi-bar stitch-bonded construction and related fastening system. A yarn system forms an arrangement of surface loops extending in stitched relation through a composite nonwoven stitching substrate incorporating at least one layer of a cellulose tissue disposed in surface covering relation to at least one layer of a nonwoven support material of polymeric fiber. Multiple layers of cellulose tissue and nonwoven support material may be used if desired.

19 Claims, 2 Drawing Sheets

(56) References Cited

U.S. PATENT DOCUMENTS

| | | | |
|---|---|---|---|
| 2005/0196581 A1* | 9/2005 | Provost | A44B 18/0011 428/85 |
| 2007/0275622 A1* | 11/2007 | Masuda | D04H 1/44 442/327 |
| 2009/0068393 A1* | 3/2009 | Homolle | D04B 21/165 428/99 |
| 2010/0015386 A1* | 1/2010 | Baldauf | A44B 18/0011 428/99 |
| 2014/0000003 A1* | 1/2014 | Ashraf | A61F 13/514 2/69 |

* cited by examiner

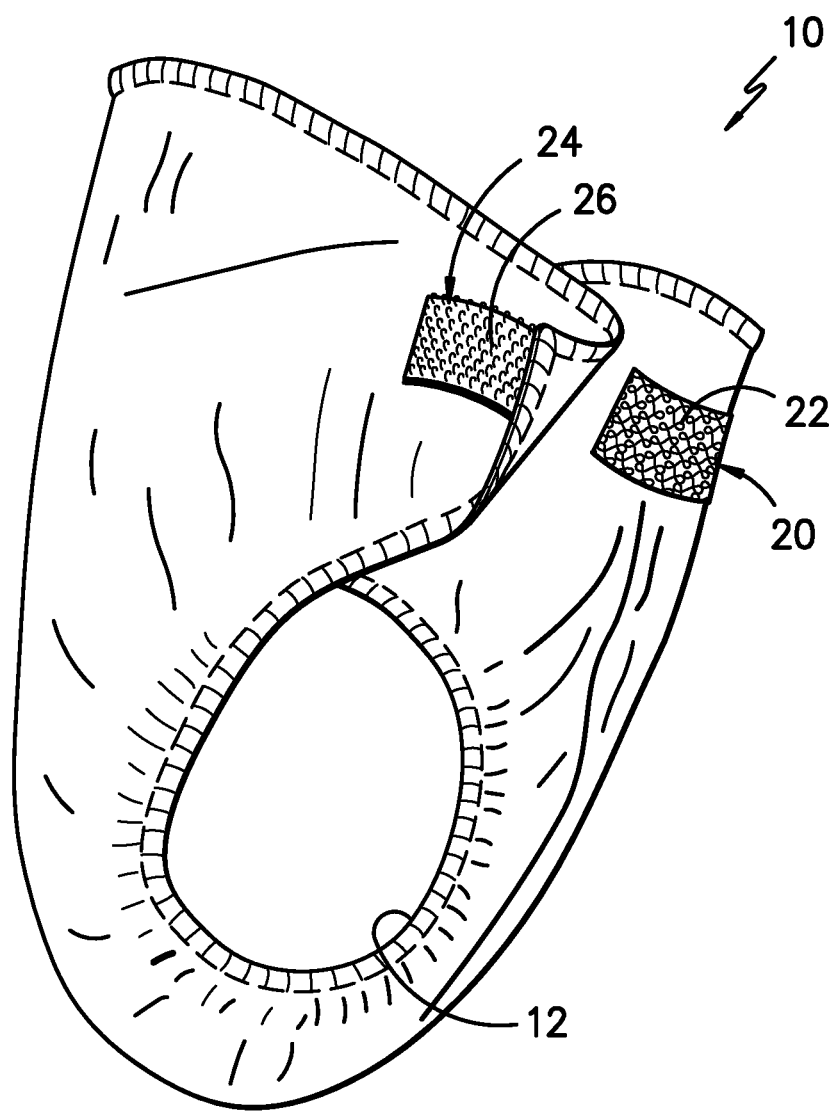
FIG. -1-

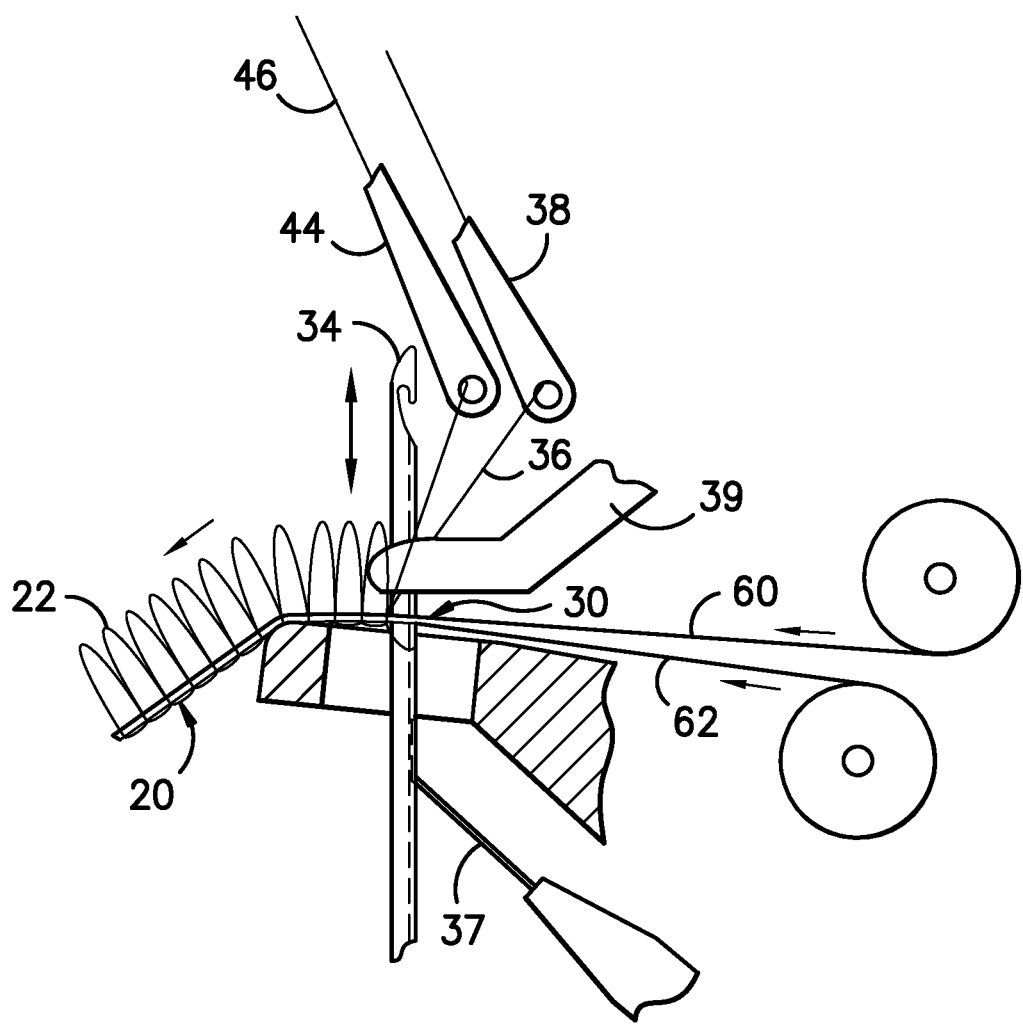
FIG. -2-

LOOP FASTENER MATERIAL FOR DIAPER AND RELATED METHOD

CROSS-REFERENCE TO RELATED APPLICATION(S)

This application claims the benefit of, and priority from. U.S. provisional Application 62/416,855 in the name of Martin Wildeman having a filing date of Nov. 3, 2016. The contents of such prior application and all documents referenced herein are hereby incorporated by reference in their entity as if fully set forth herein.

TECHNICAL FIELD

The present disclosure relates to a hook and loop fastening system, and more particularly, to a hook and loop fastening system incorporating a loop face composite material of stitch bonded construction including an arrangement of surface loops disposed across at least one surface. The loop face composite material includes a yarn system stitched through a substrate to define an arrangement of surface loops of yarn extending above a composite substrate. The loop face composite material is adapted for use as the landing zone of a tear-away fastening system for use on a diaper or other environment of use incorporating a hook and loop fastening arrangement.

BACKGROUND OF THE DISCLOSURE

Tear away or contact fastening systems are well known. Such systems incorporate two opposing segments of material which are engageable in substantially juxtaposed relation to one another. A male portion of such a contact fastening system typically incorporates a plurality of outwardly projecting hooking structures, while the female portion incorporates a plurality of outwardly projecting loop structures. Upon engagement between the two cooperating portions, the hooking structures engage the opposing loop structures thereby establishing a bond. This bond may be broken by the application of a peeling action between the two opposing portions of material thereby permitting the male and female portions to be progressively disengaged from one another. The engagement may be reactivated by simply bringing the male and female portions back into contacting juxtaposed relation with one another.

Stitch-bonding is a known process in which yarns are stitched through a substrate to form a coordinated web structure. By way of example only, and not limitation, exemplary stitch-bonding processes are disclosed in U.S. Pat. Nos. 6,855,392; 6,869,660; and 7,294,387 all of which are incorporated by reference as if fully set forth herein. In the past stitch-bonding has been used in the manufacture of loop face composite material to form the loop portion of a tear-away fastening system in a diaper using an LDPE (low density polyethylene) film as the stitching substrate. By way of example only, and not limitation, such materials are disclosed in U.S. Pat. No. 8,632,517 to Wildeman et al., the contents of which are incorporated herein by reference in their entirety.

A benefit of using a film as the stitching substrate in prior loop face composite materials is that even with the piercing of the stitch-forming needles, the resulting stitched composite maintains a low Frasier air permeability of about 25 cubic feet per minute (CFM) when measured according to ASTM D737 (the contents of which test procedure are hereby incorporated by reference as if fully set forth herein).

Maintaining a low air permeability is generally considered to be desirable in the processing of the stitch-bonded material during diaper production. By way of example, according to one exemplary diaper formation practice, a continuous roll of the loop material (ranging from about 140 mm-180 mm width) may be fed into a diaper machine and a hot melt adhesive is applied to the non-loop side of the material. The fabric then is cut into a part that the machine then adheres onto the front of the diaper. During this attachment procedure, a vacuum drum or belt is used to control and transport the cut part for assembly onto the diaper. In the event that the loop material is too permeable to air flow, the vacuum system may have difficulty in controlling the cut part, and the attachment procedure may be compromised.

While the prior use of LDPE film substrate in a stitch-bonded loop fabric inherently provides excellent performance, one potential deficiency of using a film substrate is that some users may prefer a material having a more fabric-like feel. Such materials may also be difficult to print. Accordingly a stitch-bonded loop face composite incorporating a nonwoven substrate to impart a fabric feel while maintaining a suitably low air permeability to operate with a diaper machine vacuum system would be of substantial benefit.

SUMMARY OF THE DISCLOSURE

In accordance with one exemplary feature, the present disclosure provides advantages and alternatives over the prior art by providing a composite loop face fabric which incorporates a multi-bar stitch-bonded construction and related fastening system. A yarn system forms an arrangement of surface loops extending in stitched relation through a composite substrate incorporating one or more layers of light weight cellulose tissue of the type typically used to form paper towels, napkins and the like in juxtaposed relation to one or more layers of a nonwoven support substrate material such as spunbond material, meltspun material or combinations thereof. In this regard, such combinations of spunbond material and meltspun material are commonly referred to as SMS nonwovens wherein one or more layers of meltblown nonwoven material is in sandwiched relation to one or more layers of spunbond nonwoven material. As will be appreciated, such substrate materials are referred to as SMS nonwovens, although multiple layers of meltblown nonwoven material and/or spunbond nonwoven may be used if desired. The layers of the composite substrate may be connected before stitching or may be connected by the stitchbonding procedure. The final stitched composite is characterized by a Frasier air permeability of not greater than about 130 cfm (cubic feet per minute) per square foot at a differential pressure of 0.5 inches of water when measured in accordance with ASTM D737. Such air permeability levels are suitable for use with typical diaper machine vacuum systems.

In accordance with another exemplary feature, the present disclosure provides advantages and alternatives over the prior art by providing a composite loop face fabric which incorporates a multi-bar stitch-bonded construction and related fastening system. A yarn system incorporating biodegradable yarns such as yarns formed from polylactic acid polymer ("PLA") or similar biodegradable materials forms an arrangement of surface loops extending in stitched relation through a composite substrate incorporating one or more layers of light weight cellulose tissue of the type typically used to form paper towels, napkins and the like in juxtaposed relation to one or more layers of a nonwoven substrate material such as spunbond material formed from PLA fibers or similar biodegradable materials. The layers of the composite substrate may be connected before stitching or may be connected by the stitchbonding procedure. The final stitched composite is fully biodegradable since PLA and cellulose are each biodegradable and is characterized by a Frasier air permeability of about 130 cfm per square foot or less at a differential pressure of 0.5 inches of water when measured in accordance with ASTM D737. Such air permeability levels are suitable for use with typical diaper machine vacuum systems. Of course, stitching yarns incorporating PLA or other biodegradable fibers may also be used in combination with a composite substrate incorporating one or more layers of light weight cellulose tissue in juxtaposed relation to one or more layers of a nonwoven SMS substrate material of polypropylene or the like. Likewise, polyester stitching yarns may be used in combination with a composite substrate incorporating one or more layers of light weight cellulose tissue in juxtaposed relation to one or more layers of a nonwoven substrate material such as spunbond material formed from PLA fibers or similar biodegradable materials. In each case, the final product is characterized by a Frasier air permeability of not greater than about 130 cfm per square foot at a differential pressure of 0.5 inches of water when measured in accordance with ASTM D737.

In one exemplary and non-limiting aspect, the present disclosure provides a diaper having a releasable fastening system. The fastening system includes a fastening tab with a segment of hook material having a plurality of outwardly projecting hooking elements. The fastening system further includes a segment of loop material disposed at a portion of the diaper remote from the fastening tab. The segment of loop material including a plurality of outwardly projecting loop elements is adapted to engage the hooking elements in juxtaposed contacting relation. The loop material comprises a composite sheet of stitch bonded construction including a multi-layer composite substrate with a first plurality of yarn elements extending in stitched relation through the substrate to define a ground layer of flat stitches. The loop material further includes a second plurality of yarn elements extending in stitched relation through the substrate layer to define the outwardly projecting loop elements extending above the ground layer of flat stitches. The multi-layer nonwoven composite substrate includes at least one layer of a relatively light weight cellulosic tissue in juxtaposed relation to one or more layers of a nonwoven support substrate material such as spunbond polypropylene, meltspun polypropylene, SMS polypropylene material or combinations thereof as may be desired. Other fibers such as polyester, Nylon and the like may also be used. Preferably the resultant loop material may has a weight of not greater than about 65 grams per square meter.

In another exemplary and non-limiting aspect, the present disclosure provides a diaper having a releasable fastening system. The fastening system includes a fastening tab with a segment of hook material having a plurality of outwardly projecting hooking elements. The fastening system further includes a segment of loop material disposed at a portion of the diaper remote from the fastening tab. The segment of loop material including a plurality of outwardly projecting loop elements is adapted to engage the hooking elements in juxtaposed contacting relation. The loop material comprises a composite sheet of stitch bonded construction including a multi-layer composite substrate with a first plurality of PLA yarn elements extending in stitched relation through the substrate to define a ground layer of flat stitches. The loop material further includes a second plurality of PLA yarn elements extending in stitched relation through the substrate layer to define the outwardly projecting loop elements extending above the ground layer of flat stitches. The multi-layer nonwoven composite substrate includes at least one layer of a relatively light weight cellulosic tissue in juxtaposed relation to one or more layers of a nonwoven spunbond substrate material such as spunbond PLA or the like. The resultant loop material may has a weight of not greater than about 65 grams per square meter and a Frasier air permeability of about 130 cfm per square foot or less at a differential pressure of 0.5 inches of water when measured in accordance with ASTM D737.

Other exemplary features and aspects of the disclosure will become apparent upon review of the following detailed description of preferred embodiments and practices.

BRIEF DESCRIPTION OF THE DRAWINGS

The accompanying drawings, which are incorporated in, and which constitute a part of this specification, illustrate exemplary constructions and procedures in accordance with the present disclosure and, together with the general description of the disclosure given above and the detailed description set forth below, serve to explain the principles of the disclosure wherein:

FIG. 1 illustrates a diaper incorporating a fastening arrangement utilizing cooperating hook and loop structures; and FIG. 2 illustrates schematically a two bar stitch-bonding process for selectively forming a surface loop yarn system and a cooperating ground yarn system through a substrate.

While exemplary features of the disclosure have been illustrated and are generally described above and will hereinafter be described in connection with certain potentially preferred embodiments and practices, it is to be understood that in no event is the disclosure limited to such illustrated and described embodiments and practices. On the contrary, it is intended that the present disclosure shall extend to all alternatives and modifications as may embrace the general principles of this disclosure within the full and true spirit and scope thereof.

DESCRIPTION OF THE PREFERRED EMBODIMENT(S)

Turning now to the drawings, in FIG. 1 there is illustrated a diaper 10 including a leg opening 12 and a releasable, adjustable fastening assembly. The fastening assembly incorporates a first segment of material 20 including a plurality of outwardly projecting loop elements 22 and a second segment of material 24 incorporating a plurality of outwardly projecting hooking elements 26. By the term "hooking elements" is meant elements having a geometry adapted to releasably engage the loop elements 22 upon contact. By way of example only, and not limitation, such hooking elements 26 may be configured to have a hooked terminal end and/or an enlarged terminal end such as a "mushroom" shape or the like to become engaged within the loop elements 22. Of course it is to be appreciated that the relative position of the first segment of material 20 incorporating the loop elements 22 and the second segment of material 24 incorporating the hooking elements 26 may be reversed if desired. However, in a diaper, the material forming the loop elements 22 is most typically disposed across a zone overlying a user's abdominal region as shown and will define a "landing zone" or "frontal tape" for receipt of the hooking elements 26 which are typically disposed across outwardly extending tabs.

It is to be appreciated that the length of one or both of the first and second segments of material 20, 24 may be adjusted so as to provide a desired arrangement for properly adjusting the diaper 10. By way of example only and not limitation, it is contemplated that in the illustrated arrangement wherein the first segment of material 20 incorporating the loop elements 22 is disposed across a forward portion of the diaper 10, such first segment of material 20 may extend across an extended length thereby providing an extended landing zone surface for engagement with the second segment of material 24 during the joining process. This arrangement may facilitate adjustment of the diaper 10 to users of various size.

According to the exemplary practice, the first segment of material 20 may be of a so called "stitch bonded" construction having substantially parallel rows of stitches extending through a substrate. Such materials may be formed using a multi-bar stitch bonding apparatus as illustrated schematically in FIG. 2 and the operation of which will be well known to those of skill in the art.

Referring now to FIG. 2, in the illustrated practice, a composite substrate material 30, as will be described more fully hereinafter, is conveyed to a stitch-forming position in the direction indicated by the arrows. As will be appreciated by those of skill in the art, the stitch-forming position is defined by a row of reciprocating needles 34, extending in adjacent relation to one another across the width of the composite substrate material 30 substantially transverse to the direction of movement of the composite substrate material 30. While only a single needle has been illustrated, in actual practice a large number of such needles are arranged in close relation to one another in the cross-machine direction between the fingers 39 of a sinker bar. It is contemplated that the so-called gauge or needle density in the cross machine direction and the stitch density in the machine direction may be adjusted as desired. In one exemplary embodiment, the gauge will be about 14 needles per inch and the stitch density may be about 9.2 courses per inch. However, higher and lower values may be used if desired According to the illustrated exemplary practice, two yarn systems (i.e. two bars) are used to form stitches through the composite substrate material 30. In the illustrated two bar practice, ground yarns 36 forming a first yarn system are carried through a first set of moveable yarn guides 38 manipulated by a back guide bar (not shown) for engagement with needles 34, across the width of the substrate material 30. While only a single ground yarn 36 is illustrated, it will be understood that in practice multiple ground yarns are present across the width of the stitch-forming apparatus. By way of example only and not limitation, the ground yarns 36 may have a linear density of about 20 denier to about 300 denier. One such suitable yarn for use in a diaper attachment is 40-denier/24 filament fully drawn polyester yarn. However, other yarn constructions and filament counts including monofilament may likewise be utilized if desired.

According to the potentially preferred practice, the ground yarns 36 are in a fully threaded arrangement to engage each needle. In operation, each ground yarn 36 preferably engages a single needle 34 which moves up and down in a reciprocating manner through the substrate material 30. As will be appreciated by those of skill in the art, in operation, the needle 34 engages a closing wire 37 to close the needle on the down stroke and to reopen it on the upstroke so as to form an arrangement of stitch lines running in the machine direction along the length of the substrate material. In accordance with one exemplary practice, the ground yarns 36 manipulated by the back bar are stitched in a repeating chain stitch pattern of 1,0/0,1// and do not cross between needle lines and thus do not pass over the fingers 39 of the sinker bar. According to one potentially desirable practice, the stitch lines formed by the ground yarns 36 may be sufficiently close to cover the upper surface of the composite substrate material 30.

The loop elements 22 may be formed by a loop yarn 46 threaded through moveable yarn guides 44 carried by a front guide bar (not shown). The loop yarn 46 is preferably substantially fully threaded relative to the needles 34. While only a single loop yarn 46 is illustrated for explanatory purposes, it is to be understood that in actual practice, multiple loop yarns are used across the width of the fabric. By way of example only, and not limitation, the loop yarns 46 may have a linear density of about 20 denier to about 300 denier. One such suitable yarn for use in a diaper attachment is a 40 denier/24 filament fully drawn polyester yarn. However, other yarn constructions and filament counts including monofilament may likewise be utilized if desired.

In the fully threaded arrangement, the loop yarns 44 will form a substantially continuous pattern of loop elements 22. In accordance with one exemplary practice, the loop elements 22 may be formed by passing the loop yarns 44 back and forth in a zigzag pattern between adjacent needles 34 over the fingers 39 of the sinker bar using a repeating stitch pattern of 1,0/1,2//. During the stitch-forming reciprocating action of the needles 34, the fingers 39 of the sinker bar hold the crossing segments of the loop yarns above the substrate, thereby yielding upstanding loops rather than flat stitches. By way of example only, a pile sinker height of about 2 mm may be used. However, other heights may be used if desired.

As noted previously, ground yarns 36 and loop yarns 46 are stitched through a composite substrate material 30 formed from layers of two or more different materials. In accordance with one exemplary practice, the composite substrate material 30 is formed from one or more layers of cellulose tissue 60 in layered relation with an underlying nonwoven support 62 such as a spunbond substrate or SMS nonwoven. As illustrated, the cellulose tissue 60 and the nonwoven support 62 may be delivered from separate sources and are thereafter jointed together during the stitch-bonding procedure.

By way of example only, and not limitation, one exemplary cellulose tissue 60 may be of the type used to form individual plies of paper products such as napkins, paper towels and the like. Such tissue materials typically have a mass per unit area of about 10 to 25 grams per square meter and more preferably about 16 grams per square meter. However, higher and lower weight materials may also be used. Moreover, while only a single layer of cellulose tissue 60 is illustrated, it is contemplated that multiple layers may be used if desired.

In the illustrated exemplary material, the nonwoven support 62 may be a so called "SMS" nonwoven which includes one or more interior layers of a melt blown nonwoven fibrous material formed from a suitable polymer such as polypropylene, polyester (PET), polyamide or the like disposed in sandwiched relation to one or more covering layers of spunbond nonwoven fibrous material formed from a suitable polymer such as polypropylene, polyester (PET), polyamide or the like. In one exemplary construction, the nonwoven support 62 is formed from two layers of melt-blown nonwoven polypropylene fibrous material sandwiched between two opposing layers of spunbond nonwoven polypropylene fibrous material to form an SMMS structure. However, it is likewise contemplated that a single layer of meltblown nonwoven or multiple layers of meltblown nonwoven fibrous material may be used to form structures such as SMS, SMMMS, SMMMMS, and so forth. It is also contemplated that multiple layers of spunbond nonwoven fibrous material may be used on either side if desired to form structures such as SSMSS, SSMMSS, SSMMMSS, SSMMMMSS, SSSMSSS, SSSMMSSS, SSSMMMSSS, SSSMMMMSSS and the like. Of course, such laminate arrangements are exemplary only and it is contemplated that sandwich structures having any number of layers of each material may be used as may be desired. Moreover, while all layers may be formed from the same polymer, it is likewise contemplated that different layers may be formed from different polymers if desired.

By way of example only, an adhesive bond may be present between the layers due to melt adhesion between layers and/or by use of supplemental adhesives at the layer interfaces. The nonwoven support 62 will typically have a mass per unit area of about 10 to 25 grams per square meter and more preferably about 13.5 grams per square meter. However, higher and lower weight materials may also be used.

Surprisingly, it has been found that a combination of the light weight cellulose tissue 60 and the nonwoven support 62 provides both satisfactory strength and a desirable low air permeability of less than about 130 cfm per square foot without requiring a substantial mass of material. In addition, the tissue provides a smooth opaque surface which is suitable for printing if desired.

As noted previously, the nonwoven support 62 using an SMS sandwich structure may be replaced with one or more layers of spunbond or meltspun nonwoven of polypropylene or other suitable fiber as may be desired. That is, the nonwoven support 62 would not have an alternating pattern of spunbonded and meltblown layers. Although the permeability for such a structure may be somewhat higher for a given weight, it may still be at an acceptable level.

In accordance with yet another alternative construction, it is contemplated that the cellulose tissue 60 may be replaced with an LDPE film or other suitable polymer layer overlying a light weight spunbond or meltspun nonwoven. In this regard, such a film may be either extrusion coated onto the nonwoven or may be connected to the nonwoven during the stitch-bonding procedure. In either event, extremely low permeability may be achieved at low weights.

In accordance with still another exemplary practice, the ground yarns 36 and/or loop yarns 46 may be formed from a biodegradable material such as a polylactic acid ("PLA") polymer or the like. Likewise, the nonwoven support 62 may be formed from a PLA spunbond. As will be appreciated, in the event that the ground yarns 36, loop yarns 46 and nonwoven support 62 are each formed from PLA, the entire resulting structure will be formed from biodegradable materials (i.e. cellulose and PLA) thereby providing potential environmental benefits.

Regardless of the construction being used, the final stitched weight of the first segment of material 20 is preferably not greater than about 65 grams per square meter, and is more preferably about 25 to about 55 grams per square meter. By way of example only, one exemplary embodiment incorporates 40 denier polyester stitching yarns, a 16 gram per square meter cellulose tissue, and a 13.5 gram per square meter SMMS polypropylene nonwoven support to yield a 48.5 gram per square meter product for use as the first segment of material 20. Of course, higher or lower weights may likewise be used for any of the components if desired.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A diaper having a releasable fastening system, the fastening system comprising:
 a fastening tab including a segment of hook material having a plurality of outwardly projecting hooking elements; and
 a segment of loop material of stitch bonded construction disposed at a portion of the diaper remote from the fastening tab, the segment of loop material including a plurality of outwardly projecting loop elements adapted to engage the hooking elements in juxtaposed contacting relation, wherein the loop material comprises a composite sheet of stitch bonded construction including a multi-layer nonwoven stitching substrate with a first plurality of yarn elements extending in stitched relation through the stitching substrate to define a ground layer of flat stitches, and wherein the composite sheet of stitch bonded construction further includes a second plurality of yarn elements extending in stitched relation through the stitching substrate in crossing relation between parallel needle lines to define said plurality of outwardly projecting loop elements extending above the ground layer of flat stitches, wherein the multi-layer nonwoven stitching substrate comprises at least one layer of a cellulose tissue disposed in surface covering relation to at least one layer of a nonwoven support material of polymeric fiber, wherein the loop material has a weight of not greater than 65 grams per square meter and a Frasier air permeability of not greater than 130 cubic feet per minute per square foot at a differential pressure of 0.5 inches of water when measured in accordance with ASTM D737.

2. The diaper as recited in claim 1, wherein the segment of loop material is disposed at a position on the diaper overlying a user's abdominal region.

3. The diaper as recited in claim 2, wherein the first plurality of yarn elements extends in stitched relation through the substrate layer to define a plurality of parallel stitch lines of flat stitches extending along the machine direction of the sheet material.

4. The diaper as recited in claim 3, wherein the parallel stitch lines of flat stitches cooperatively form a ground layer substantially covering an upper surface of the substrate layer.

5. The diaper as recited in claim 1, wherein the first plurality of yarn elements are polyester yarns and the second plurality of yarn elements are polyester yarns, and wherein said at least one layer of a nonwoven support material loop material has a mass per unit area of about 10 to 25 grams per square meter and comprises at least one layer of meltblown polymeric nonwoven disposed in sandwiched relation between layers of spunbond polymeric nonwoven.

6. The diaper as recited in claim 1, wherein the first plurality of yarn elements are polyester yarns and the second plurality of yarn elements are polyester yarns, and wherein said at least one layer of a nonwoven support material loop material consists essentially of a spunbond polypropylene nonwoven.

7. The diaper as recited in claim 1, wherein the first plurality of yarn elements are PLA yarns and the second plurality of yarn elements are PLA yarns, and wherein said at least one layer of a nonwoven support material loop material consists essentially of a spunbond PLA nonwoven.

8. The diaper as recited in claim 1, wherein the loop material has a weight of less than 50 grams per square meter.

9. The diaper as recited in claim 1, wherein said at least one layer of a cellulose tissue is adhesively bonded to said at least one layer of a nonwoven support material.

10. The diaper as recited in claim 1, wherein said at least one layer of a cellulose tissue is secured to said at least one layer of a nonwoven support material by said first plurality of yarn elements without adhesive bonding.

11. A diaper having a releasable fastening system, the fastening system comprising:
a fastening tab including a segment of hook material having a plurality of outwardly projecting hooking elements; and
a segment of loop material of stitch bonded construction disposed at a portion of the diaper remote from the fastening tab, the segment of loop material including a plurality of outwardly projecting loop elements adapted to engage the hooking elements in juxtaposed contacting relation, wherein the loop material comprises a composite sheet of stitch bonded construction including a multi-layer nonwoven stitching substrate with a first plurality of yarn elements extending in stitched relation through the stitching substrate to define a ground layer of flat stitches, and wherein the composite sheet of stitch bonded construction further includes a second plurality of yarn elements extending in stitched relation through the stitching substrate in crossing relation between parallel needle lines to define said plurality of outwardly projecting loop elements extending above the ground layer of flat stitches, wherein the multi-layer nonwoven stitching substrate comprises at least one layer of a cellulose tissue having a mass per unit area of 10 to 25 grams per square meter disposed in surface covering relation to at least one layer of a nonwoven support material of polymeric fiber having a mass per unit area of 10 to 25 grams per square meter, wherein the loop material has a weight of not greater than 65 grams per square meter and a Frasier air permeability of not greater than 130 cubic feet per minute per square foot at a differential pressure of 0.5 inches of water when measured in accordance with ASTM D737.

12. The diaper as recited in claim 11, wherein the first plurality of yarn elements extends in stitched relation through the substrate layer to define a plurality of parallel stitch lines of flat stitches extending along the machine direction of the sheet material.

13. The diaper as recited in claim 12, wherein the parallel stitch lines of flat stitches cooperatively form a ground layer substantially covering an upper surface of the substrate layer.

14. The diaper as recited in claim 11, wherein the first plurality of yarn elements are polyester yarns and the second plurality of yarn elements are polyester yarns, and wherein said at least one layer of a nonwoven support material loop material has a mass per unit area of about 10 to 25 grams per square meter and comprises at least one layer of meltblown polypropylene nonwoven disposed in sandwiched relation between layers of spunbond polypropylene nonwoven.

15. The diaper as recited in claim 11, wherein the first plurality of yarn elements are polyester yarns and the second plurality of yarn elements are polyester yarns, and wherein said at least one layer of a nonwoven support material loop material has a mass per unit area of 10 to 25 grams per square meter and consists essentially of a spunbond polypropylene nonwoven.

16. The diaper as recited in claim 11, wherein the first plurality of yarn elements are PLA yarns and the second plurality of yarn elements are PLA yarns, and wherein said at least one layer of a nonwoven support material loop material has a mass per unit area of 10 to 25 grams per square meter and consists essentially of a spunbond PLA nonwoven.

17. The diaper as recited in claim 11, wherein the loop material has a weight of less than 50 grams per square meter.

18. The diaper as recited in claim 11, wherein said at least one layer of a cellulose tissue is adhesively bonded to said at least one layer of a nonwoven support material.

19. The diaper as recited in claim 11, wherein said at least one layer of a cellulose tissue is secured to said at least one layer of a nonwoven support material by said first plurality of yarn elements without adhesive bonding.

* * * * *